United States Patent [19]

Cardarelli

[11] 4,299,613

[45] Nov. 10, 1981

[54] CONTROLLED RELEASE OF TRACE NUTRIENTS

[75] Inventor: Nathan F. Cardarelli, Barberton, Ohio

[73] Assignee: Environmental Chemicals, Inc., Wauconda, Ill.

[21] Appl. No.: 51,102

[22] Filed: Jun. 22, 1979

Related U.S. Application Data

[63] Continuation-in-part of Ser. No. 14,118, Feb. 22, 1979, which is a continuation-in-part of Ser. No. 5,174, Jan. 22, 1979, which is a continuation-in-part of Ser. No. 916,570, Jun. 19, 1978, Pat. No. 4,166,111.

[51] Int. Cl.$^3$ ............................................. A01N 25/00
[52] U.S. Cl. ....................................... 71/64 F; 521/63; 47/DIG. 10; 71/27
[58] Field of Search .................. 71/64 G, 64 F, 27, 1, 71/64 D; 47/58, 57.6, DIG. 10; 521/63; 264/44, 344, 345

[56] References Cited

U.S. PATENT DOCUMENTS

| | | | |
|---|---|---|---|
| 2,791,496 | 5/1957 | Rice | 71/64 G X |
| 2,797,985 | 7/1957 | Larson | 71/1 X |
| 2,891,355 | 6/1959 | Nelson | 71/64 G X |
| 3,059,379 | 10/1962 | Attoe | 71/64 F X |
| 3,372,019 | 3/1968 | Fox | 71/64 F |
| 3,794,478 | 2/1974 | Dirksen | 71/1 |
| 4,019,890 | 4/1977 | Fujita et al. | 71/64 F |
| 4,111,684 | 9/1978 | Thomas et al. | 71/64 F X |

FOREIGN PATENT DOCUMENTS

| | | | |
|---|---|---|---|
| 68127 | 12/1965 | Australia | 71/27 |
| 44-28457 | 11/1969 | Japan | 71/27 |
| 49-43776 | 11/1974 | Japan | 47/DIG. 10 |

OTHER PUBLICATIONS

Powell; Controlled Release Fertilizers; 1968; Noyes Development Corp.; pp. 181–182.

*Primary Examiner*—Ferris H. Lander
*Attorney, Agent, or Firm*—Oldham, Oldham, Hudak & Weber Co.

[57] ABSTRACT

Compositions of and a method for preparing polymeric formulations that gradually, continuously and uniformly release various compounds over a long period of time in ionic form that are well recognized as essential to the growth of agricultural commodities. The compounds, such as inorganic salts of varying water solubilities, are monolithically incorporated in a thermoplastic polymeric matrix usually of two thermoplastic polymers, for example, a copolymer of poly(ethylene-vinyl acetate) or a copolymer of ethylene and propylene. Release is generally conditioned upon the presence of moisture and is proportional to the moisture content of soil treated with the subject invention. Release rate is tailored to a given desirable condition by regulation of the free volume and/or porosity within the polymer matrix and through dispenser geometry. Free volume is maintained at the level conducive to agent release such as through the use of free volume modifying secondary thermoplastic additives such as low density polyethylene; and porosity is controlled through the use of porosity enhancing agents appropriately termed porosigens. Said porosigens can be the low or moderate soluble salts such as the carbonates, bicarbonates, sulfates, phosphates, nitrates, etc.; of the alkali metals, the alkaline earths, or ammonium. Upon exposure to moisture, water ingress into the dispensing pellet removes said porosigen through dissolution processes thus creating a porous network permitting water contact with the incorporated nutrient molecules and their gradual egress in said water over a period of time such as for about a couple months to four years, or longer.

25 Claims, No Drawings

CONTROLLED RELEASE OF TRACE NUTRIENTS

CROSS-REFERENCE

This application is a continuation-in-part of my copending application entitled "FLOATING CHIP DISPENSER" filed on Feb. 22, 1979 as U.S. Ser. No. 14,118, which in turn is a continuation-in-part of my earlier copending application entitled "A METHOD AND COMPOSITION FOR THE LONG TERM CONTROLLED RELEASE OF A NON-PERSISTENT ORGANOTIN PESTICIDE FROM AN INERT MONOLITHIC THERMOPLASTIC DISPENSER" filed on Jan. 22, 1979 as U.S. Ser. No. 5,174, which in turn is a continuation-in-part of an application bearing the same title which was filed on June 19, 1978 as U.S. Ser. No. 916,570, now U.S. Pat. No. 4,166,111.

BACKGROUND OF THE INVENTION

The present invention relates to the incorporation of the soluble or sparingly soluble compounds of various elements recognized as essential to plant health and growth in a modified thermoplastic dispensing pellet, powder, granule, or other convenient dispensing form. Such compounds are salts or oxides of well recognized trace elements vital to plant nutrition. Said salts or oxides upon contact with water release zinc, iron, copper, boron, manganese, molybdenum, magnesium, cobalt and selenium in an ionic form as a water solution. Said plants, through natural processes, absorb the trace nutrient during uptake of the nutrient enriched water. Release, being largely moisture dependent, is self-regulatory. During the growing season, wherein soil moisture is readily available, trace nutrient release is continuous and uniform. When moisture is not present, the plants generally do not grow and said nutrients are not released, thus avoiding loss of nutrient.

Heretofore, agronomists and nutritionists have recognized the vital and essential function of various elements needed in minute quantities by growing plants. Such elements have been termed "trace nutrients." Their functions vary, some being essential to the photosynthetic process or being a critical component in various enzyme systems. In general, the complete lack of a given trace element precludes plant growth. For instance, Western Australia would not support agricultural field crops prior to the introduction of zinc into the soil. In most instances where trace nutrients are utilized, the normal soil content is too low for proper nutrition and plants cultivated in said soils are generally more susceptible to disease, show poor growth characteristics and consequently crop yields are low.

It is common practice to supplement trace element poor soils by adding the needful material directly or as an additive in bulk nutrient applications containing those substances classified as "fertilizers", i.e., nitrogen, potassium and phosphorus. Most agricultural commodities require trace element soil supplement for optimum growth and thus maximum yield. Such agricultural commodities include field crops such as wheat, alfalfa, potatoes, clover, tobacco, pineapple, soy beans, sugar, beets, cotton, corn, barley, oats, rice, and the like; citrus fruits; nuts, such as pecans peanuts, coffee, cocoa, walnut, almond; fruits such as apples, pears, cherries, plums, peaches; vegetables, such as beans, peas, cauliflower, carrots, lettuce, tomatoes, cabbage, and the like; and, forestry commodities such as pine trees, and pasture grasses. In the latter case, elements essential to animal growth such as zinc, iron, copper and selenium are ingested by domestic animals consuming said pasture grasses as forage. Lack of trace amounts of critical elements in the cow, sheep, goat and swine lead to deficiency diseases and thus decreased output of meat, milk and wool.

It is probable that lack of application of trace nutrients in U.S. agricultural activities could lead to substantial declines in food production. It is also likely that proper use of trace elements in soils lacking adequate quantities of said materials, such as in vast reaches of Africa, would lead to a dramatic increase in agricultural productivity.

Heretofore, in a typical utilization system, relatively high dosages of trace nutrients are added periodically to the soil. A number of disadvantages, ameliorated by this invention, occur. Said nutrients are of necessity water soluble salts or oxides else the treated plant cannot absorb them. Being water soluble, a large proportion of material applied, perhaps 80 percent or more, is lost from the root zone via natural processes such as percolation in the vertical direction to earth strata below the effective range of the root structure or washed beyond said root range through the movement of ground waters in the horizontal direction. In addition, the type of soil plays a profound role in the trace nutrient contact and ingestion processes. Alkaline soils and/or clay type soils generally complex the added nutrient chemical thus creating insoluble ligands of no value to the nutrient deficient plant. The rate of soil intervention in the nutrition process varies with pH and type, but is an extremely important negative factor.

Relatively massive amounts of the trace elements must thus be applied to overcome natural loss processes and mechanisms. This leads to two distinct and severe disadvantages. In general, treatment must be afforded before such growing season and sometimes followed by one or more retreatments during that season. It is unusual for one treatment to last over any great length of time and consequently, effort is expended and chemicals are purchased repeatedly by the agriculturist at frequent intervals with a concomitant economic factor increasing the cost of foodstuff production. Probably of even greater significance is that massive treatment early in the season leads to luxurious consumption (i.e., consumption beyond real plant needs) early in the growing season with rapidly depleting chemical availability during the middle and late growing season. It is generally recognized that the uniform availability of the trace nutrient in appropriate day-by-day quantities optimizes yield.

The use of controlled-release trace nutrients of the present invention will overcome the luxury consumption, inadequate consumption cycle thus giving greater crop yield, will reduce the total amount of trace nutrient needed, and will also greatly extend between treatment times, from one to two, three, or more years, possibly five or ten years, depending on agricultural practices and natural circumstances (crop rotation and so on).

It is well known that biocidal materials can be incorporated in a polymeric matrix and caused to release at a rate efficacious with pest destruction. U.S. Pat. No. 3,417,181 teaches that organotin toxicants can be dissolved in an elastomer-type matrix and caused to release through a diffusion-dissolution mechanism when exposed to water. The crux of this seminal invention was keyed to the necessity of the agent being soluble in the polymer. Similarly, U.S. Pat. Nos. 3,590,119; 3,426,473; 3,851,053; and 3,639,583 extend the scope of the art to embrace new formulations encompassing different elastomers, specific release regulants that effect the diffusion path length and the like, but again the key concept is the necessity of agent solubility in the elastomer. Agents incorporated are organic pesticides and the generic matrix type is elastomers such as natural rubber, styrene-butadiene rubber, and the like. In contrast, U.S. Pat. No. 4,012,221 teaches that inorganic copper salts capable of being released into water are incorporated in a moderately crosslinked elastomer in which the copper salts are insoluble.

It is well known to the compounding art that agents not soluble within a polymeric matrix will not move at an efficacious rate through said matrix to said matrix surface and thus enter the ambient environment.

Almost all organic pesticidal agents lack solubility in thermoplastic matrixes. Similarly, inorganic pesticidal agents are likewise insoluble in known thermoplastic or thermosetting polymers.

One method of causing an insoluble organic agent to emit from a plastic dispensing unit is to use a third phase material that is (1) soluble in some extent in said plastic and (2) will carry said organic agent in solution or serve as a migratory pathway for said agent to reach the surface of said dispenser. It is, of course, recognized that the incorporated agent must reach the plastic/external environment interface to have any effect on organisms inhibiting the external environment. U.S. Pat. Nos. 2,956,073 and 3,116,201 describe the use of plasticizers as carrier elements. In an improvement on such patents, U.S. Pat. Nos. 3,705,938 and 3,864,468 teach that surface loss from a plasticized matrix is subject to control through the use of a regulating membrane at said surface.

The controlled-release art has been generally confined to the incorporation and release of insecticides, bactericides, molluscicides and other toxic materials of an organic nature from an elastomer, wherein solubility is essential or a plastic, wherein an additive carrier material is critical. Microencapsulation processes wherein an inner core of the toxic agent is surrounded by a polymeric matrix is well known to the pest control art. In general, release is effected by the rupture of the enveloping membrane and/or the passage of water through the porous membrane structure, said water path serving as a means of egress for said pesticide which reaches in this manner the external environment.

Little work has been hitherto performed in the development of efficacious long lasting fertilizing systems. U.S. Pat. No. 3,748,115 teaches that plant nutrients can be bound in a matrix of synthetic rubber, waxes, asphalt, and the like. In this work, four critical elements of the invention are set forth. The fertilizer, emphasizing bulk materials and not trace nutrient, must be uniformly dispensed in a hydrophobic binding element. The dispensing unit must be cylindrical in shape. Said cylinder must be partially coated with a water-insoluble, water-permeable exterior membrane. A portion of the cylinder must be non-coated with said membrane. U.S. Patent 3,520,651 extends this art to teach that more than one nutrient can be incorporated in similar dispensing commodities.

In contrast, the subject invention is related to trace nutrient elements, the binding matrix need not be hydrophobic, the dispenser can take any shape although the granule or pellet is preferred, and no exterior membrane is utilized.

Of course, fertilizing materials have long been compounded with various binders to facilitate dispersal and, in some cases, to prolong availability by slowing the rate of solution in water through precluding immediate nutrient element contact with water. U.S. Pat. No. 3,336,129 teaches that the use of small amounts of water insoluble copolymers and terpolymers of ethers, substituted ethers, ethylene oxide and the like will serve as carriers for fertilizing materials, said copolymers and terpolymers must be crosslinked. Materials are comprised of polymer+fertilizer+water+soil components and the plant is grown within this medium.

Also, fertilizers such as urea can be coated in a granular form as taught in U.S. Pat. No. 3,336,155 thus retarding solution in ground waters. U.S. Pat. No. 3,276,857 teaches that a fertilizer can be encapsulated with asphalt or various waxes and thus emission into the environment is slowed.

SUMMARY OF THE INVENTION

Accordingly, it is an object of the present invention to provide for the slow release of plant trace nutrients.

It is another object of the present invention to provide for the slow release of trace nutrients, as above, wherein said trace nutrients are contained in a polymer matrix.

It is a further object of the present invention to provide for the slow release of trace nutrients, as above, wherein said trace nutrients include zinc, iron, copper, boron, manganese, molybdenum, magnesium, cobalt, and selenium.

It is an additional object of the present invention to provide for the slow release of trace nutrients, as above, wherein said trace nutrients, when applied to soil and through water dissolution, is readily available to various plants such as crops, citrus fruits, nuts, vegetables, pasture grasses, trees, and the like through natural processes such as absorption of the trace nutrient during uptake of the nutrient-enriched water.

It is still another object of the present invention to provide for the slow release of trace nutrients, as above, wherein said polymer matrix is made from a copolymer of ethylene-vinyl acetate, a copolymer of ethylene-propylene, a low density polyethylene, and combinations thereof.

It is a still further object of the present invention to provide for the slow release of trace nutrients, as above, wherein said polymer matrix is made from a copolymer of ethylene-vinyl acetate, a copolymer of ethylene-propylene, and combinations thereof.

It is yet another object of the present invention to provide for the slow release of trace nutrients, as above, wherein said polymer matrix contains a porosigen compound.

It is yet another object of the present invention to provide for the slow release of trace nutrients, as above, wherein said porosigen desirably is soluble or sparingly soluble in water such that said trace nutrient is released over a time period from a few months to a few years.

These and other objects of the present invention will become apparent from the specification.

In general, a slow release trace nutrient composition, comprises: 100 parts of a polymer matrix; said polymer matrix made from a compound selected from the class consisting of an ethylenevinyl acetate copolymer, an ethylene-propylene copolymer, a low density polyethylene, and combinations thereof; the amount by weight of said ethylene constituent in said ethylene-vinyl acetate copolymer ranging from about 60 percent to about 95 percent, the weight average molecular weight of said ethylenevinyl acetate copolymer ranging from about 40,000 to about 400,000; the amount by weight of said ethylene constituent in said ethylene-propylene copolymer ranging from about 30 percent to about 75 percent, the weight average molecular weight of said ethylene-propylene copolymer ranging from about 50,000 to about 250,000; said low density polyethylene having a density of from about 0.90 to about 0.94 grams per cc and a weight average molecular weight of from about 100,000 to about 400,000; and a plant trace nutrient contained in said polymer matrix, the amount of said trace nutrient being such that said trace nutrient is slowly released when said polymer matrix is in contact with an aqueous environment.

DESCRIPTION OF THE PREFERRED EMBODIMENTS

According to the concepts of the present invention, trace nutrients are slowly and controllably released to soil to improve plant growth and yield over an extended period of time. This result is obtained by incorporating the trace nutrient into a polymer matrix. Additionally, the matrix can contain soluble or sparingly soluble porosigen compounds therein.

In my prior copending continuing applications, my invention related to the sustained release of various pesticides, from a polymer matrix, against such aquatic pests such as mosquito larva, the aquatic larva form of parasites, molluscan hosts of trematode parasites, and the like. The pesticide such as an organotin compound, and the like, could be contained in a polymer matrix which either sank or floated. The exact nature of the various pesticides and porosigens contained within the polymer matrix, as well as the concepts of the inventions therein, are set forth in my previous continuing applications which are hereby fully incorporated by reference.

Now it has been found that trace nutrients can slowly be released when contacted by an aquatic environment or moisture, such as rain or moisture in the soil, often times by only the copolymer matrix when the trace nutrient itself is a porosigen, and most always released when using the porosigen compounds set forth below. A polymer matrix binder of the present invention is an ethylene-vinyl acetate copolymer. Such a copolymer is readily available in commerce and the amount by weight of the ethylene units, based upon the total weight of the copolymer, ranges from about 60 percent to about 95 percent with a range of from about 80 percent to about 93 percent being preferred. The weight average molecular weight of the copolymer generally ranges from about 40,000 to about 400,000 and preferably from about 75,000 to about 300,000. Desirably, the copolymer has an ASTM Test #D1238 melt flow index of from about 6 to about 12 and preferably from about 7 to about 11 and a Vicat softening point of from about 70° C. to about 95° C. Since, apparently, the ethylene repeating units in the copolymer act as a regulator with regard to pore size, higher amounts of the ethylene constituent will result in slower release times.

Additionally, another polymer matrix or binding agent of the present invention which can be utilized alone or in combination with said ethylene-vinyl acetate copolymer, that is from 1 percent to 99 percent and preferably from about 35 percent to about 60 percent is an ethylene-propylene copolymer having a weight average molecular weight of from about 50,000 to about 250,000 with a preferred range of from about 100,000 to about 200,000. The percent by weight of the ethylene units can generally vary from about 30 percent to about 75 percent, and preferably from about 45 to about 75 percent by weight, based upon the total weight of the copolymer. The melt flow index of the ethylene-propylene copolymer can generally range from about 15 to about 45, and preferably from about 20 to about 32 according to ASTM Test #D1238 at 190°, 21600 gm,gm/10 minutes.

Additionally, it has been found that low density polyethylene can be used by itself as a polymer matrix. Preferably, the polyethylene matrix has been found useful to provide a long release deviation when blended with the ethylene-vinyl acetate copolymer or the ethylene-propylene copolymer, or combinations thereof. By low density polyethylene, it is meant a polyethylene having a density of from about 0.90 to 0.94 g/cc and a weight average molecular weight of from about 100,000 to about 400,000. The melt flow index of the low density polyethylene may be similar to said ethylene-vinyl acetate copolymer, that is from about 5 to about 14, and preferably from about 7 to about 11, as in Microthene MN 718 (manufactured by U.S.I. Chemicals). Melt flow=8.5 g/10 minutes according to ASTM Test #D1238. Although generally a lower release rate is obtained, the melt flow index of the low density polyethylene may be low, that is from about 1.0 to about 5.0 as when Microthene MN 703 is utilized (a low density polyethylene manufactured by USI Chemicals) having a melt index of 1.2 g/10 minutes according to ASTM Test #D1238. Similarly, a low density polyethylene having a high melt flow index such as from about 11 to 25 may be utilized and results in a greater release rate. Thus, depending upon the rate of release, various amounts of low density polyethylene may be utilized, as from 1 percent to 99.9 percent. Generally, to obtain desirable release rates, the amount of homopolyethylene utilized may range from about 30 percent to about 75 percent and, preferably, from about 40 percent to about 60 percent by weight based upon the total weight of the polymer matrix blend, that is the weight of the ethylene-vinyl acetate copolymer and/or the weight of the ethylene-propylene copolymer with the low density polyethylene.

The various trace elements utilized are generally in the form of salts or oxides, which are readily available, desirably low in cost, and are not highly deliquescent. It is noted that the term "salts" includes the various hydrates thereof, that is the mono-, the di-, the tri-, the tetra-, the penta-, the hexa-, the hepta-, etc. Should the salt not exist in a non-hydrate form, the most common forms are meant. With regard to zinc-containing compounds which may be utilized as trace nutrients, they include the following: zinc sulfate, zinc chloride, zinc carbonate, zinc oxide, zinc phosphate, zinc chlorate, zinc nitrate, the various existing hydrates thereof, and the like. Typical copper trace nutrient compounds include copper sulfate, copper carbonate, copper oxide, copper oxychloride, copper nitrate, copper phosphate; various copper complexes such as tetramines, diamines; the various existing hydrates thereof, and the like. Typical iron trace nutrient compounds include iron chloride, iron sulfate, iron oxide, the various existing hydrates thereof, and the like. Typical manganese trace nutrient compounds include manganese oxide, manganese sulfate, manganese chloride, manganese nitrate; the various existing hydrates thereof, and the like. Typical boron trace nutrient compounds include boric acid, sodium biborate; the various existing hydrates thereof, and the like. Typical molybdenum trace nutrient compounds include molybdenum oxide, sodium molybdate, potassium molybdate, the various existing hydrates thereof, and the like. Typical cobalt trace nutrient compounds include cobalt sulfate, cobalt chlorate, cobalt nitrate; the various existing hydrates thereof, and the like. Typical selenium trace nutrient compounds include sodium selenate, selenium dioxide, selenium trioxide, selenium oxychloride, selenium disulfide, selenium sulfur oxide, and the like. Typical magnesium compounds include magnesium carbonate, magnesium sulfate, magnesium nitrate, magnesium acetate, magnesium oxide, magnesium chloride, magnesium ammonium chloride, magnesium phosphate, magnesium sulfite; the various existing hydrates thereof, and the like.

Desirably, the amount of trace nutrient released by the polymer matrix is such to make the plant grow or to supplement the environment. That is, the soil is supplemented such that the plant's intake is supplemented, preferably to an extent of its normal amount of the particular trace nutrient required. Naturally, the exact amount will vary depending upon several factors such as the lack of the specific trace nutrient in the soil, the various types of soil, the intake requirement of a particular trace nutrient for a specific plant or crop. Thus, the actual amount will vary from site to site, depending upon soil characteristics and the plant species involved. Accordingly, the exact demands for a particular trace nutrient of the present invention will naturally and inherently vary greatly. In order to achieve a desirable amount of trace nutrient required for a particular or specific soil and type of plant, several methods may be utilized. For example, a much larger amount of the polymer matrixes containing the particular trace nutrient or nutrients may be released, i.e., a larger number of pounds per acre. Another method is simply to utilize a formulation having a higher release rate of a particular trace nutrient. Still another method is to use a formulation having a higher amount of trace nutrient content therein. Yet another method relates to utilizing larger particles, that is, granules or chips. Additionally, other variations may also be utilized. As an approximate rule of thumb, the formulation can contain from about 1 percent to about 60 percent by weight of a particular trace nutrient ion, based upon the total weight of the formulation. A desirable amount is from about 2 percent to about 50 percent, with a more desirable amount being from about 4 percent to about 40 percent. The amount of trace nutrient compound which usually exists as a salt or oxide ranges from about 10 to about 160 parts by weight based upon 100 parts by weight of the polymer, desirably from about 25 to about 125 parts, and preferably from about 50 to about 100 parts by weight.

Generally, a particular soil is usually deficient in one or two trace nutrients. However, in some instances, it may require a few or even several trace nutrients. According to the present invention, a plurality of trace nutrients can be contained within a particular polymer matrix in various amounts suitable to meet the demands of the particular crop or plant desired. Thus, a so-called "one-shot approach" may be utilized instead of applying several applications of polymer matrixes, each containing a different trace nutrient.

Release of the trace nutrient is generally confined to the soil environment. However, the plants allowed to assimilate the trace nutrients will not grow unless the soil contains some degree of moisture. Thus, moisture is utilized as a transporting material in dispensing the trace nutrient. Therefore, it is essential that the formed polymer matrix be amenable to water egress and ingress. Thus, the porosity of the polymer matrix becomes important to the slow release process. It is generally believed that the enhancement of microporosity (free volume) as well as macroporosity of the polymer matrix is important to the present invention. Porosity can be imparted by various chemical compounds termed porosity enhancing agents or "porosigens." However, depending upon the type of polymer utilized as well as the type of compound utilized as a trace nutrient which, itself, often times serves as a porosity agent, it is thus not always necessary to utilize such an agent. For example, trace nutrient compounds such as a chloride, copper sulfate, iron sulfate, iron chloride, manganese sulfate, manganese oxide, manganese chloride, boric acid, sodium biborate, sodium molybdate, cobalt sulfate and sodium selenate can be utilized without the aid of a porosigen. Of course, a co-porosigen of a low water solubility would increase the rate released and a co-porosigen having a higher water solubility would increase the rate even more.

Generally, the amount of trace nutrient and the optional porosigen is such that release occurs over a period in excess of one month to a couple, a few, and even several years. Although largely dependent upon soil conditions and plant intake required, an amount of porosigen is utilized such that the daily release rate of the trace nutrient varies from about 0.001 to about 4 percent by weight per day based upon the total weight of the trace ion available in a particular matrix. A desired daily release rate is from about 0.001 or, more desirably, 0.01 percent to about 3 percent of the total amount of trace nutrient ion available, and more desirably from about 0.90 percent to about 1.6 percent per day, and preferably from about 0.30 percent to about 1.1 percent per day.

As noted above, the type of porosigen will vary depending upon the desired release rate sought. Should a relatively low increase rate be sought over the release rate level effected by only the polymer and the trace nutrient, a number of moderate or low solubility compounds can be utilized as a porosity-inducing agent. By moderate solubility, it is meant that the solubility is approximately 0.1 grams or less per 100 grams of water, whereas by a low solubility compound, it is meant that it has a solubility of approximately 0.01 grams or less per 100 grams of water.

Generally, any compound which is inert with respect to the polymer matrix and the trace nutrient can be utilized, as a porosigen. By inert, it is meant that the porosigen does not chemically react with the polymer or the trace nutrient. Additionally, the porosigen is also not damaging or harmful to the environment in terms of toxicity. Thus, the porosigen can be any compound which is set forth in the Handbook of Chemistry and Physics, 1977–78 Edition, published by the Chemical Rubber Co., which is hereby fully incorporated by reference, and meets the above requirements with regard to solubility and non-harmful to the environment.

A suitable class of an inert porosigen compound includes the inorganic salts or the hydrates thereof, or oxides. The cation of such a salt may generally be any of the alkaline metals and preferably any of the non-toxic alkaline earth metals, Column 1A and 2A, respectively, of the Periodic Table. Additionally, various other metals may be utilized such as iron, nickel, zinc, tin, silver and the like. The anion portion of the salt may generally be any negative charge entity, as the various carbonates, the various bicarbonates, the various nitrates, nitrites, or nitrides, the various sulfates, sulfites, or sulfides, the various phosphates, phosphites, or phosphides, including the ortho, pyro, hypo, variations thereof, and the like. Generally, the sulfates, sulfites and sulfides are preferred as anions, with carbonates being highly preferred. Moreover, as noted above, the anion may be an oxide of the metal. Specific examples of coleachants include magnesium carbonate, magnesium sulfide, magnesium phosphide, magnesium oxide, calcium carbonate, calcium bicarbonate, calcium nitride, calcium oxide, calcium phosphate, calcium phosphite, calcium sulfide, calcium sulfite, iron carbonate, iron sulfate, iron sulfide, iron sulfite, nickel carbonate, nickel sulfide, zinc carbonate, zinc oxide, zinc sulfide, zinc sulfite, tin sulfide, tin oxide, silver carbonate, silver oxide, silver sulfide, silver sulfite, sodium bicarbonate lithium phosphate, beryllium oxide, strontium carbonate, strontium sulfate, and strontium sulfite. Additionally, silicon dioxide may also be utilized. Magnesium carbonate, strontium carbonate, ammonium carbonate, and barium carbonate are preferred, with calcium carbonate being highly preferred.

When it is desirable to use a porosigen compound having a soluble porosigen, that is a solubility greater than 0.1 grams per 100 grams of water, generally any inert and non-environmental harmful compound can be utilized which has a solubility of from about 0.1 to about 1.0 gram and desirably from about 1.0 to about 100 grams per 100 grams of water. Examples of such soluble compounds are set forth in the Handbook of Chemistry and Physics, 1977-78 Edition, published by the Chemical Rubber Company which is hereby fully incorporated by reference. Specific examples include sodium carbonate and sodium bicarbonate.

Generally, the halogen salts of the alkalin metals and the alkalin earth metals, Column 1A and 2A, respectively, of the Periodic Table, as well as of nickel, iron, zinc, tin and silver, which have a solubility of at least 0.1 grams/100 grams of water, and preferably the chloride salts thereof can also be utilized. The Handbook of Chemistry and Physics, 1977-78 Edition, Supra. is hereby fully incorporated as to such specific compounds since the list is rather extensive. Additionally, ammonia as a cation constitutes another class of salts with specific examples being ammonium bromide, ammonium carbonate, ammonium bicarbonate, ammonium chlorate, ammonium chlorite, ammonium chloride, ammonium fluoride, ammonium sulfate, and the like. Additionally, sodium silicate can also be used. Of this group, sodium bicarbonate, sodium carbonate, silicon dioxide, sodium silicate, and ammonium sulfate are preferred. Moreover, inert liquids compatible with and dispersible in the polymer matrix such as the lower and glycerol glycols may be utilized, especially ethylene glycol.

Generally, suitable amounts of a porosigen range from 0.1 to 70 parts by weight based upon 100 parts by weight of polymer matrix, desirably from about 1.0 parts to about 30 parts, and preferably from about 2.0 parts to about 12 parts.

The slow release trace nutrient composition or formulation can contain, in addition to the above-mentioned components, various well known and conventional additives to enhance dispersion, add color, aid in processing, or to alter density. For example, zinc stearate may be utilized as a dispersant in suitable amounts as from 0.2 parts to about 5 or 10 parts by weight per 100 parts by weight of polymer with about 1 or 2 parts being preferred.

The composition can also contain suitable amounts of an attractant-porosigen such as from about 2 to about 25 parts of soy oil or lecithin when it is desired that a particular type of animal eat the nutrient, e.g., cattle, with 4 to 16 parts being desirable. Additionally, various amounts, i.e., 1 to 30 or 2 to 12 parts of carbon black may be utilized as a regulant.

In order to form a suitable thermoplastic dispenser which releases suitable amounts of the trace nutrient, it is desirable that the particle sizes of the various components be relatively small. For example, it is desirable that the various trace nutrients have a Tyler mesh size of roughly 100 or greater (i.e., a particle size smaller than 100 mesh) and preferably smaller than 200 mesh. Accordingly, a particle size range for the porosigen is generally the same. The particle size of the ethylene-vinyl acetate copolymer, the polyethylene, and the ethylene-vinyl acetate copolymer is roughly about 50 to 200 Tyler mesh. Since the composition is made by heating and melting the polymer, the polymer size prior to formation of the matrix is not very important.

The slow release trace nutrient composition is prepared by mixing the trace nutrient with the copolymer and/or the low density polyethylene either alone or with the porosigen in suitable proportions as indicated above in any conventional mixing apparatus along with various additives such as colorants, dispersants, and the like. The mixture is then coalesced by heating at least above the softening point and preferably above the melting point of the polymer and partitioned for use in any suitable size or shape, for example, chip, pellet, etc. Thus, the mixture may be added to a conventional extruder where it is molded at from about 120° C. to about 220° C. in a suitable form such as a ribbon which can be cut into pellets, etc.

Before numerous examples are presented to disclose various embodiments and best mode of the invention, a few general rules are noted with regard to determining the effect of any formulation with regard to release of a trace nutrient. In general, the incorporation of a porosigen agent will cause the release of more trace nutrient on a daily basis. Conversely, the incorporation of a low density polyethylene will moderate or reduce the daily release, especially if the polyethylene has a low melt flow index (for example, 5.0 or less). If the trace nutrient is fairly soluble in water, for example, 1.0 or greater, or if a very low release rate is desired and the polymer is either the ethylene-propylene copolymer or the ethylene-vinyl acetate copolymer, a porosigen is not required. Additionally, the ethylene-vinyl acetate copolymer gives better release than the ethylene-propylene copolymer. As well appreciated by one skilled in the art, many factors can effect the results such as the actual particle or chip size of the polymer matrix, surface area of the polymer matrix or chip, and the like, so that the general rules are just that, general rules.

The invention will be better understood by reference to the following examples.

Typical formulations for the controlled release of zinc ions are set forth hereinbelow.

EXAMPLE I—ZINC SULFATE FORMULATIONS

Several formulations of zinc sulfate in various plastic matrices and without porosigen additives are depicted in the following table:

TABLE I

| INGREDIENT | FORMULATION (PARTS) | | | | | | | | | | |
|---|---|---|---|---|---|---|---|---|---|---|---|
| | 1-A | 1-B | 1-C | 1-D | 1-E | 1-F | 1-G | 1-H | 1-I | 1-J | 1-K |
| EVA 763[1] | 50 | 40 | 50 | 50 | 50 | 50 | 100 | — | — | 50 | 50 |
| LDPE 718[2] | 40 | 50 | 40 | 40 | 40 | 40 | — | 100 | — | 40 | 40 |
| LDPE 703[3] | — | — | — | — | — | — | — | — | 100 | — | — |
| Zinc Stearate[4] | 2 | 2 | 2 | 2 | 2 | 2 | 2 | — | 2 | 2 | 2 |
| Zinc Sulfate[5] | 80 | 80 | 80 | 80 | 60 | 80 | 80 | 80 | 80 | 80 | 80 |
| Am. Sulfate[6] | — | — | 5 | 10 | 5 | 5 | 5 | 5 | 5 | — | — |
| Ethylene Glycol[7] | — | — | — | — | — | 2 | — | — | — | — | — |
| Sodium Bicarbonate[8] | — | — | — | — | — | — | — | — | — | 5 | 10 |

[1] Ethylene vinylacetate copolymer (U.S. Industrial Chemical Co. code MU763, Melt Index 9.0)
[2] Low density polyethylene (U.S. Industrial Chem. Co. code MN718, Melt Index 8.5)
[3] Low Density polyethylene (U.S. Industrial Chem. Co. code MN703, Melt Index 1.2)
[4] Zinc stearate used as a dispersant
[5] Zinc sulfate monohydrate, 200 mesh, Sherwin Williams Co., 361-S ($ZnSO_4 \cdot H_2O$)
[6] Ammonium sulfate (porosigen)
[7] Ethylene glycol (porosigen)
[8] Sodium Bicarbonate (porosigen)

The materials in Table I were immersed in mineral free distilled water. Said water was analyzed at periodic intervals for zinc ion in accordance with the standard diphenylthiocarbazone method (ASTM 25.077).

After each zinc determination, immersion water was discarded and zinc free water added to the test containers in order to forstall the development of solution equilibrium. Analyses were performed at 1, 2, 7, 14, 21 and 30-day intervals and once monthly thereafter for 4 to 12 months.

Steady state conditions typified by a continuous emission rate were achieved, usually by the seventh day past immersion. After initial addition to water, a preliminary high emission is observed as the zinc sulfate molecules on or very close to the surface are dissolved by and lost into the surrounding waters.

The following steady state emission rates were determined:

| FORMULATIONS | EMISSION RATE % AGENT LOSS PER DAY |
|---|---|
| 1-A | 0.04 |
| 1-B | 0.08 |
| 1-C | 0.83 |
| 1-D | 0.38 |
| 1-E | 0.34 |
| 1-F | 0.76 |
| 1-G | 0.37 |
| 1-H | 0.0 |
| 1-I | 0.13 |
| 1-J | 0.37 |
| 1-K | 1.2 |

Several salient features underlying the uniqueness of this invention can be noted. (1) Other factors being constant, comparison of 1-G using ethylene-vinyl acetate alone as the matrix element (0.37 percent per day emission) with formulation 1-H using low density polyethylene (melt index 8.5) as the sole matrix element (0.0 percent per day emission) and formulation 1-I using only low density polyethylene (melt index 1.2) indicates that polyethylene alone provides a lower and, in an agricultural context, inferior loss rate.

It is evident that the use of a porosity-enhancing agent such as ammonium sulfate and sodium bicarbonate, among others, greatly increases emission rate.

Ethylene glycol in conjunction with ammonium sulfate greatly enhances porosity growth and hence increased emission. In contrast, ethylene glycol alone provides only a small degree of porosity enhancement.

Under the test conditions used, specifically the fact that immersion water was of slightly acidic pH, the use of sodium bicarbonate as the porosigen provided considerably higher emission rates. Compare formulation 1-J having approximately 3 percent porosigen (0.37 percent per day emission) with 1-K having approximately 6 percent porosigen (1.2 percent per day emission).

EXAMPLE II—ZINC OXIDE FORMULATIONS

The low water solubility of zinc oxide results in much lower omission rates as compared with the highly water soluble zinc sulfate material of the previous example.

A few formulations are depicted below:

TABLE II

| Ingredient | FORMULATION (parts) | | | | |
|---|---|---|---|---|---|
| | 2-A | 2-B | 2-C | 2-D | 2-E |
| EVA 763 | 50 | 50 | 50 | 100 | 50 |
| LDPE 718 | 40 | 40 | 40 | — | — |
| LDPE 703 | — | — | — | — | 40 |
| Zinc Stearate | 2 | 2 | 2 | 2 | 2 |
| Zinc Oxide | 80 | 80 | 80 | 80 | 80 |
| Ammonium Sulfate | — | 5 | — | — | 5 |
| Sodium Bicarbonate | — | — | 5 | — | — |

Periodic zinc analysis using the procedure previously described provided the following results:

| FORMULATION | EMISSION RATE % AGENT LOSS PER DAY |
|---|---|
| 2-A | 0.005 percent |
| 2-B | 0.014 percent |
| 2-C | 0.017 percent |
| 2-D | 0.017 percent |
| 2-E | 0.018 percent |

Comparing 2-A (no porosigen) to 2-B (3 percent ammonium sulfate) again indicates the enhancement of porosity, and hence emission, observed by the use of such additives. Also comparing 2-D (using ethylene-vinyl acetate copolymer alone) having a 0.017 percent per day emission with 2-A, wherein ethylene-vinyl acetate copolymer is modified with polyethylene, indicates the moderating effect of said polyethylene. Importantly, it is observed that when ethylene-vinyl acetate copolymer (melt index 9.0) is modified with polyethylene of melt index 8.5 (MN 718), emission is present.

EXAMPLE III—ZINC CHLORIDE FORMULATIONS

Several formulations using highly water soluble zinc chloride salt (432 g/100 g $H_2O$ compared to 100 g/100 g $H_2O$ zinc sulfate soluble) were similarly prepared and evaluated for zinc emission rate. Formulations and emission rates are shown below.

TABLE III

| Ingredient | FORMULATION (parts) | | |
|---|---|---|---|
| | 3-A | 3-B | 3-C |
| EVA | 100 | — | — |
| MN 718 | — | 100 | — |
| MN 703 | — | — | 100 |
| Zinc Stearate | 2 | 2 | 2 |
| Zinc Chloride | 80 | 80 | 80 |
| Ammonium Sulfate | 5 | — | — |
| Emission Rate % loss per day | 2.1% | 0.18% | 0.90% |

In this instance, the extreme water solubility of zinc chloride is such that it, in essence, acts as its own porosigen, porosity growth arising as the zinc ion is rapidly dissolved into the surrounding water. Although the highest emission is is from ethylene-vinyl acetate copolymer as expected, polyethylene will also bind and emit, though at a much reduced rate.

EXAMPLE IV—ZINC CARBONATE FORMULATIONS

Under practical use conditions, the very low emission observed with zinc oxide materials and the high rates expected with zinc chloride may not be optimal in many instances. Likewise, zinc sulfate having considerable water solubility may not be acceptable in an agricultural situation of high rainfall and/or prolonged heavy ground moisture, rice paddy for instance. Thus, a relatively low solubility of controlled-release zinc carbonate might be of greater utility. Formulations and emission rates are depicted in the following table:

TABLE IV

| Ingredient | FORMULATION (Parts) | | | | |
|---|---|---|---|---|---|
| | 4-A | 4-B | 4-C | 4-D | 4-E |
| MU 763 | 50 | 50 | 50 | 100 | 100 |
| MU 718 | 40 | 40 | 40 | — | — |
| Zinc Stearate | 2 | 2 | 2 | — | 2 |
| Zinc Carbonate | 50 | 80 | 80 | 80 | 80 |
| Ethylene Glycol | 25 | — | — | — | — |
| Sodium Bicarbonate | — | — | — | — | — |
| Ammonium Sulfate | — | — | 5 | — | — |
| Emission Rate % Loss per day | 0.0% | 0.014% | 0.038% | 0.029% | 0.040% |

It is observed that even large amounts of ethylene glycol without another porosigen also present does not enhance porosity. Comparing 4-D using MU 763 only as the binding matrix without a porosigen to essentially the same material with about 3 percent ammonium sulfate (4-C), the porosity enhancement in the latter case leads to a higher emission rate.

BIOASSAY EVALUATION

Due to the high variability of composition and nature of soils, and the lack of a standard soil type, the tests described herein as typifying the invention have been performed in water since standardization is possible. It is recognized that (1) the end use of the formulations of this invention are in application to soil for (2) the increase in the yield of specific agricultural commodities. In this respect, a fast emission zinc sulfate formulation and a slow emission zinc carbonate formulation were evaluated in zinc poor soil as a means of ascertaining merit therein. Soy bean plants were grown in seven inch diameter pots in the laboratory, said pots each containing 1,300 grams of soil. Two hundred milliliters of water were added once daily. Results are shown below:

GROWTH RATE OF SOY BEANS IN ZINC POOR SOIL TREATED WITH CONTROLLED RELEASE ZINC FORMULATIONS

| COMPOUND | POT DOSAGE | AVERAGE POST GERMINATION STEM GROWTH | ZINC CONTENT (Leachate) |
|---|---|---|---|
| 1-D[1] | 1 g | 2.75 cm/day | 0.0015 ppm/day |
| | 0.5 g | 1.94 cm/day | 0.0011 ppm/day |
| | 0.2 g | 1.40 cm/day | 0.0007 ppm/day |
| | 0.1 g | 1.14 cm/day | 0.0002 ppm/day |
| Control | 0.0 g | 1.09 cm/day | 0.00008 ppm/day |
| 4-E[2] | 1 g | 3.13 cm/day | 0.0003 ppm/day |
| | 0.5 g | 2.20 cm/day | 0.0004 ppm/day |
| | 0.2 g | 2.14 cm/day | 0.0002 ppm/day |
| | 0.1 g | 1.95 cm/day | 0.0002 ppm/day |
| Control | 0.0 g | 1.07 cm/day | 0.00008 ppm/day |

As can be observed in examining the bioassay data, a definite enhancement in soy bean growth is present due to the use of controlled release zinc formulations. It is further noted that in this instance the zinc carbonate material gave better growth characteristics in that less of the emitted agent was lost through leaching. To further illustrate the importance of the distinction between fast and slow emission formulations, zinc analysis was performed on plant tissue and soil after 56 days of growth. Results are shown below:

| FORMULATION | DOSAGE | Zn++ (Soil) | Zn++ (Leaf) | Zn++ (Root) |
|---|---|---|---|---|
| 1-D[1] | 1.0 g | 0.075 ppm | 0.03 ppm | 0.10 ppm |
| | 0.5 g | 0.060 ppm | 0.05 ppm | 0.09 ppm |
| | 0.2 g | 0.050 ppm | 0.03 ppm | 0.08 ppm |
| | 0.1 g | 0.050 ppm | 0.04 ppm | 0.07 ppm |
| Control | 0.0 | 0.00 | 0.05 ppm | 0.04 ppm |
| 4-E[2] | 1.0 g | 0.01 ppm | 0.08 ppm | 0.05 ppm |
| | 0.5 g | 0.01 ppm | 0.05 ppm | 0.03 ppm |
| | 0.2 g | 0.04 ppm | 0.08 ppm | 0.02 ppm |
| | 0.1 g | 0.02 ppm | 0.08 ppm | 0.01 ppm |
| Control | 0.0 | 0.005 ppm | 0.05 ppm | 0.01 ppm |

[1] 43 percent zinc sulfate and 6 percent porosigen; rapid release.
[2] 44 percent zinc carbonate and no porosigen providing a very slow release.

Whereas the higher emission rate of 1-D leads to a greater soil concentration at any given instant than that seen with 4-E; the leaf content is greater and hence plant growth, in the latter instance. Under differing moisture conditions, the values might well reverse.

EXAMPLE V-COPPER EMISSION

Several copper salts and oxides were incorporated in plastic matrices and the release rates measured in demineralized water using the procedure previously described. The bicinchoninate method of determining copper ion content was used.

COPPER SULFATE MONOHYDRATE MATERIALS ($CuSO_4 \cdot H_2O$)

A number of formulations containing copper sulfate monohydrate were prepared in accordance with the following recipes. Unlike zinc formulations, it was discovered that an ethylene-propylene thermoplastic (Vistalon 702, melt index 27, product of Exxon Chemical Co.), when modified by a low density polyethylene, provided a superior release rate.

TABLE V

| Ingredient | 5-A | 5-B | 5-C | 5-D | 5-E | 5-F | 5-G | 5-H | 5-I |
|---|---|---|---|---|---|---|---|---|---|
| EPM 702 | 100 | — | — | — | — | 50 | 100 | — | 50 |
| LDPE 718 | — | 100 | 40 | — | — | 50 | — | 100 | 50 |
| LDPE | — | — | — | — | 50 | — | — | — | — |
| EVA 763 | — | — | 50 | 100 | 50 | — | — | — | — |
| Zinc Stearate | 2 | 2 | 2 | 2 | 2 | 2 | 2 | 2 | 2 |
| Copper Sulfate Monohydrate | 80 | 80 | 80 | 80 | 80 | 80 | 80 | 80 | 100 |
| Ammonium Sulfate | 5 | 5 | — | 5 | — | — | — | — | 5 |

Copper release rate in water was found to be as follows:

| Formulation | Release Rate % copper ion/day | Remarks |
|---|---|---|
| 5-A | 0.19% | EMP 702, with $(NH_4)_2SO_4$ additive as a porosigen |
| 5-B | 0.19% | LDPE 718, with $(NH_4)_2SO_4$ additive as a porosigen |
| 5-C | 0.026% | EVA 736/LDPE 718, no porosigen |
| 5-D | 0.15% | EVA 763 with $(NH_4)_2SO_4$ additive as a porosigen |
| 5-E | 0.37% | EVA 763/LDPE 703, no porosigen |
| 5-F | 0.28% | EPM 702/LDPE 718, no porosigen |
| 5-G | 0.002% | EPM 702, no porosigen |
| 5-H | 0.0021% | LDPE 718, no porosigen |
| 5-I | 0.31% | EPM 702/LDPE 718 with $(NH_4)_2SO_4$ additives as the porosigen |

It is evident that the addition of a porosity enhancing agent, ammonium sulfate, greatly increases the loss rate of copper ion. When a LDPE is used, whose melt index varies greatly from that of EVA, enhanced release is obtained, for example, EVA 763 of a melt index 9.0 modified with LDPE 718 of melt index 8.5, as with compound 5-C displays a very slow copper ion emission, whereas EVA 763 of melt index 9.0 modified with LDPE 703 of melt index 1.2, as with compound 5-E has a much higher emission rate.

EXAMPLE VI—COPPER CARBONATE EMITTING FORMULATIONS

Formulations were prepared containing very low solubility copper carbonate as the copper ion source. Recipes are shown below:

TABLE VI

| Ingredient | 6-A | 6-B | 6-C | 6-D |
|---|---|---|---|---|
| EPM 702 | 50 | 100 | — | — |
| LDPE 718 | 50 | — | — | — |
| LDPE 703 | — | — | — | — |
| EVA 763 | — | — | 100 | 50 |
| Zinc Stearate | 2 | 2 | 2 | 2 |
| Copper Carbonate | 80 | 80 | 80 | 80 |
| Ammonium Sulfate | — | — | — | — |

Measured loss rates over a 120-day period are shown below with other pertinent information:

| Formulation | Loss Rate % $Cu^{++}$/day | Matrix | Melt Indices | Porosigen |
|---|---|---|---|---|
| 6-A | 0.0021% | EPM 702/LDPE 718 | 27/8.5 | none |
| 6-B | 0.0033% | EPM 702 | 27 | none |
| 6-C | 0.0042% | EVA 763 | 9.0 | none |
| 6-D | 0.0017% | EVA 763/LDPE 703 | 9.0/1.2 | none |

It is again noted that the use of a low density polyethylene modifier lowers the copper emission rate.

EXAMPLE VII—COPPER OXYCHLORIDE FORMULATIONS

Several controlled-release copper formulations were prepared utilizing $Cu_2(OH)_3Cl$ as the copper source. It was discovered that the principles previously enumerated similarly held for this material incorporated in thermoplastics. Note the following recipe comparison.

TABLE VII

| Ingredient | 7-A | 7-B |
|---|---|---|
| LDPE 718 (M.I. = 8.5) | 50 | — |
| EPM 702 (M.I. = 27) | 50 | 100 |
| Zinc Stearate | 2 | 2 |
| $Cu_2(OH)_3Cl$ | 80 | 80 |
| Ammonium Sulfate | 5 | 5 |
| Loss Rate % $Cu^{++}$/day | 0.021% | 0.0057% |

It is again observed that emission rate is enhanced when LDPE is used to modify the EPM matrix.

EXAMPLE VIII—CUPROUS OXIDE FORMULATIONS

Cuprous oxide having extremely low water solubility was incorporated in thermoplastic matrices and loss rate measured as depicted below.

TABLE VIII

| INGREDIENT | 8-A | 8-B | 8-C | 8-D | 8-E | 8-F | 8-G |
|---|---|---|---|---|---|---|---|
| LDPE 718 | 50 | 50 | — | — | 100 | 100 | — |
| EPM 702 | 50 | 50 | 100 | 100 | — | — | — |
| LDPE 703 | — | — | — | — | — | — | 50 |
| EVA 763 | — | — | — | — | — | — | 50 |
| Zinc Stearate | 2 | 2 | 2 | 2 | 2 | 2 | 2 |
| Cuprous Oxide | 80 | 80 | 80 | 80 | 80 | 80 | 80 |

TABLE VIII-continued

| INGREDIENT | 8-A | 8-B | 8-C | 8-D | 8-E | 8-F | 8-G |
|---|---|---|---|---|---|---|---|
| (NH$_4$)$_2$SO$_4$ | — | 5 | — | 5 | 5 | — | 5 |
| Loss Rate % Cu/day | 0.0028 | 0.0031 | 0.0023 | 0.0027 | 0.0037 | 0.0027 | 0.0010 |

Although emmission rates are quite low again, it is observed that said rate is enhanced through the use of a porosigen.

It is duly noted that emission rate of copper ion from the aforementioned formulations is temperature dependent. When soil conditions are cold and plant growth absent, the wasteful emission of copper is drastically reduced, while as the growing season progresses with warming weather, copper release increases to fully satisfy, when appropriate dosages are used, the needs of the crops. The following data taken as water emission rate at several temperatures exemplifies this phenomenon.

| RELEASE OF Cu++ FROM 5-I (Accumulative % Release, average of replicates) | | | |
|---|---|---|---|
| Time (days) | 90° F. | 72° | 40° F. |
| 1 | 6.4% | 5.5% | 4.6% |
| 5 | 14.0% | 7.5% | 6.3% |
| 10 | 14.9% | 9.9% | 6.35% |
| 20 | 17.5% | 12.5% | 6.65% |
| 31 | 26.9% | 13.2% | 7.1% |
| 45 | 31.4% | 15.5% | 7.55% |
| 60 | 32.4% | 18.6% | 7.6% |
| 87 | 38.7% | 23.8% | 7.7% |
| 118 | 41.75% | — | 8.1% |
| 158 | 45.6% | — | 8.4% |

EXAMPLE IX—IRON EMISSION

Various water soluble or sparingly water iron salts or oxides can be incorporated in ethylene vinyl acetate copolymers and low density polyethylene and blends thereof, and upon exposure to moisture caused to release iron ion at a controllable rate. Iron bearing chemicals utilizable include ferric chloride, ferrous sulfate, ferric oxide, ferric ammonium citrate, ferrous oxide, and the like, excepting those materials that decompose at extrusion temperatures such as ferric nitrate and ferric ammonium sulfate. Recipes for several formulations are shown below with extrusion conditions.

TABLE IX

| Ingredient | 9-A | 9-B | 9-C | 9-D | 9-E |
|---|---|---|---|---|---|
| LDPE 718 | 50 | 25 | — | 50 | 50 |
| EPM 702 | — | 25 | — | 50 | 50 |
| EVA 763 | — | — | 50 | — | — |
| Zinc Stearate | 1 | 1 | 1 | 2 | 2 |
| FeCl$_3$ . 6H$_2$O | 25 | — | — | — | — |
| FeSO$_4$ . 7H$_2$O | — | 50 | 50 | — | — |
| Fe$_2$O$_3$ | — | — | — | 80 | 80 |
| Ammonium Sulfate | — | — | — | 5 | — |
| Extrusion | | | | | |
| Barrel Temp. | 400° F. | 420° F. | 400° F. | 370° F. | 390° F. |
| Die Temp. | 400° F. | 400° F. | 400° F. | 390° F. | 410° F. |

Loss rate[1] is demineralized water averaged over the post immersion period from day 8 to day 151 is as follows:

| 9-A | 0.052% Fe release per day |
| 9-B | 0.17% Fe release per day |
| 9-C | 0.216% Fe release per day |
| 9-D | 0.0017% Fe release per day |
| 9-E | 0.0010% Fe release per day |

[1]Iron content in water is determined by the ferrozine method, L.L.Stookey, Anal. Chem. 42(7), 779, 1970.

EXAMPLE X—MANGANESE FORMULATIONS

Controlled-release manganese emittors were prepared in accordance with the principles outlined herein. Manganese chloride, manganese sulfate and manganese dioxide were used as the agents. Several illustrative recipes are presented below:

TABLE X

| | (parts by weight) | | | | | | | |
|---|---|---|---|---|---|---|---|---|
| Ingredient | 10-A | 10-B | 10-C | 10-D | 10-E | 10-F | 10-G | 10-H |
| EVA 763 | 100 | — | 25 | 50 | 50 | 50 | 25 | — |
| LDPE 718 | — | — | 20 | — | — | — | 20 | — |
| LDPE 703 | — | — | — | — | — | — | — | 50 |
| EPM 702 | — | 50 | — | — | — | — | — | — |
| Zinc Stearate | 1 | 1 | 1 | 1 | 1 | 1 | 1 | 1 |
| Manganese Sulfate[1] | — | 51 | 51 | 50 | 60 | — | — | — |
| Manganese Chloride[2] | — | — | — | — | — | 25 | 30 | 30 |
| Manganese Dioxide | 80 | — | — | — | — | — | — | — |
| Ammonium Sulfate | — | — | — | 5 | — | — | — | — |

[1]MgSO$_4$ . H$_2$O
[2]MgCl$_2$ . 4H$_2$O

Said formulations were immersed in water and manganese release determined[1] periodically as depicted below. It is noted that manganese dioxide having a very low solubility possesses a correspondingly low release rate-approximately 0.001 percent total manganese per day.

[1]Manganese in water is determined by the tetraphenyl arsonium chloride method. The Analyst 87, 435, June 1962.

| Release Rate of Manganese Compounds in Water | | |
|---|---|---|
| Formulation | Initial Mn Loss (30 days) | Loss Rate; % Loss/Day Day 31 to Day 122 |
| 10-B | 48.2% | 0.18% |
| 10-C | 52.2% | 0.27% |
| 10-D | 43.0% | 0.35% |
| 10-E | 52.9% | 0.27% |
| 10-F | 46.9% | 0.085% |
| 10-G | 54.2% | 0.06% |
| 10-H | 21.6% | 0.047% |

Both manganese sulfate and manganese chloride formulations show high initial loss over the first 30 days or so immersion. After that time, a steady state situation is reached. It is noted that the manganese sulfate emitting materials show a higher loss rate due to the greater water solubility of this agent. Formulation 10-D, an ethylene vinyl acetate copolymer matrix using ammonium sulfate as a porosigen exhibits the greatest degree of release.

EXAMPLE XI—CONTROLLED RELEASE BORON MATERIALS

Boron emitting materials were prepared in accordance with the principles outlined herein. Several such compounds are depicted below. Boric acid and sodium biborate, both being highly water soluble are preferred over other boron salts. Sodium bicarbonate was used as the porosigen.

TABLE XI

| Ingredient | Formulation | | | |
|---|---|---|---|---|
| | 11-A | 11-B | 11-C | 11-D |
| Vistalon 703 | 60 | 100 | — | — |
| LDPE 718 | 40 | — | — | — |
| EVA 763 | — | — | 100 | 100 |
| Zinc Stearate | 1 | 1 | 1 | 1 |
| Boric Acid (Na$_2$B$_4$O$_7$) | 50 | 50 | 50 | 50 |
| Sodium Bicarbonate | — | — | — | 2 |

| | 11-E | 11-F |
|---|---|---|
| Vistalon 702 | — | — |
| LDPE 718 | 50 | — |
| EVA 763 | 40 | 100 |
| Zinc Stearate | 1 | 2 |
| Boric Acid (Na$_2$B$_4$O$_7$) | 50 | 75 |
| Sodium Bicarbonate | — | — |

| | 11-G | 11-H | 11-J | 11-K | 11-L |
|---|---|---|---|---|---|
| Vistalon 702 | 60 | 100 | — | — | — |
| LDPE 718 | 40 | — | — | 50 | — |
| EVA 763 | — | — | 100 | 40 | 100 |
| Zinc Stearate | 1 | 1 | 1 | 1 | 2 |
| Na$_2$B$_4$O$_7$ | 50 | 50 | 50 | 50 | 75 |
| NaHCO$_3$ | — | — | 2 | — | — |

Immersion in water indicated the following release rates.

| Formulation | Release Rate (%/Day) | Remarks |
|---|---|---|
| BORIC ACID GROUP | | |
| 11-B | 0.130% | Vistalon 702 matrix |
| 11-A | 0.135% | Vistalon 702 modified with low density polyethylene |
| 11-F | 0.321% | EVA 763 matrix |
| 11-D | 0.321% | EVA 763 with NaHCO$_3$ as a porosigen (no effect) 5.78% boron content |
| 11-C | 0.378% | EVA 763 containing 5.85% boron content |
| 11-E | 0.722% | EVA 763 modified with low density polyethylene to provide much higher release rate 6.27% boron content |
| SODIUM BIBORATE GROUP | | |
| 11-L | 0.390% | EVA 763, no modification, contains 9.22% boron. |
| 11-K | 0.552% | EVA 763, modified with low density polyethylene, contains 7.72% boron |
| 11-J | 0.765% | EVA 763 with a porosigen, contains 7.14% boron |
| 11-G | 0.63% | Ethylene-propylene copolymer modified with low density polyethylene, with 7.12% boron |
| 11-H | 0.66% | Ethylene-propylene copolymer with no modification, with 7.21% boron |

Boron in water was determined by the method described in APHA Standard Methods 13 Ed. p. 72, 1971.

EXAMPLE XII—CONTROLLED RELEASE MOLYBDENUM MATERIALS

Controlled release molybdenum formulations were prepared in accordance with the recipes shown below:

TABLE XII

| Ingredient | Formulation No. | | | | | |
|---|---|---|---|---|---|---|
| | 12-A | 12-B | 12-C | 12-D | 12-E | 12-F |
| Vistalon 702 | 50 | — | — | — | — | — |
| LDPE 718 | 50 | 100 | — | — | — | — |
| Zinc Stearate | 2 | 2 | 1 | 1 | 1 | 2 |
| MoO$_3$ | 75 | 75 | 75 | 50 | 50 | — |
| EVA 763 | — | — | 100 | 100 | — | — |
| LDPE 703 | — | — | — | — | 75 | 100 |
| Na$_2$MoO$_4$ | — | — | — | — | — | 75 |

| Ingredient | Formulation No. | | | | |
|---|---|---|---|---|---|
| | 12-G | 12-H | 12-I | 12-J | 12-K |
| Vistalon 702 | 100 | 100 | 50 | 50 | 50 |
| Zinc Stearate | 1 | 2 | 1 | 2 | 2 |
| Na$_2$MoO$_4$ | 50 | 75 | 50 | 75 | 75 |
| LDPE 718 | — | — | 50 | 50 | 50 |
| (NH$_4$)$_2$SO$_4$ | — | — | — | 3 | — |
| NaHCO$_3$ | — | — | — | — | 3 |

Initial 24-hour release and average daily release after release is shown below. Molybdenum content in water was determined using the technique in *Analytical Chemistry* 25(9), 1363, 1953.

| Formulation | Mo. Content (1%) | Initial 24-Hour Release | Daily Release Rate (Day 7 through Day 30) |
|---|---|---|---|
| 12-A | 28.2 | 0.38% | 0.06% |
| 12-B | 28.2 | 0.63% | 0.09% |
| 12-C | 28.2 | 0.80% | 0.06% |
| 12-D | 22.0 | 0.69% | 0.04% |
| 12-E | 26.4 | 0.67% | 0.03% |
| 12-F | 19.8 | 1.26% | 0.09% |
| 12-G | 15.4 | 15.9% | 1.00% |
| 12-H | 19.7 | 20.3% | 1.18% |
| 12-I | 15.4 | 17.8% | 1.81% |
| 12-J | 19.4 | 33.8% | 1.45% |
| 12-K | 19.4 | 34.5% | 1.63% |

The effects of lower water solubility of MoO$_3$, (0.1 g/100 g cold water), as compared to Na$_2$MoO$_4$, (44 g/100 g cold water) can readily be seen through comparing compounds 12-A through 12-E containing MoO$_3$ with compounds 12-F through 12-K wherein Na$_2$MoO$_4$ in LDPE shows the relatively small initial loss rate in comparison with formulations 12-G through 12-K utilizing an ethylene-propylene matrix with or without an LDPE modifier. Examining of 12-H (19.7% Na$_2$MoO$_4$) and 12-G (15.4% Na$_2$MoO$_4$) it is seen that the loss rate is partially dependent upon the total agent loading. Comparison of compounds 12-C (28.2% MoO$_3$) and 12-D (22.0% MoO$_3$) one notes the same effect. Whereas 12-G (15.4% Na$_2$MoO$_4$ in Vistalon 702) provides a 1.00% per day release in water, 12-I (15.4% Na$_2$MoO$_4$) wherein Vistalon 702 is modified with LDPE 718 a much higher, 1.81% per day, loss rate is indicated. Interestingly, compounds 12-J and 12-K, both using a porosigen additive, show extremely high initial loss rate of 33.8% and 34.5% for the first 24 hours post immersion, respectively. In this instance, the use of a porosigen is contraindicated.

EXAMPLE XIII—CONTROLLED RELEASE COBALT MATERIALS

Controlled release cobalt formulations, using cobalt sulfate as the agent, were prepared in accordance with the recipes shown below.

TABLE XIII

| Ingredient | \multicolumn{9}{c}{Formulation No.} |
|---|---|---|---|---|---|---|---|---|---|
| | 13-A | 13-B | 13-C | 13-D | 13-E | 13-F | 13-G | 13-H | 13-I |
| Vistalon 702 | 60 | 60 | — | — | — | — | — | — | — |
| LDPE 718 | 40 | 40 | 100 | — | — | — | — | — | — |
| LDPE 703 | — | — | — | — | 100 | — | — | — | — |
| EVA 763 | — | — | — | 100 | — | 100 | 100 | 100 | 100 |
| Zinc Stearate | 1 | 1 | 1 | 1 | 1 | 1 | 1 | 1 | 1 |
| $CoSO_4 \cdot 7H_2O$ | 50 | 75 | 50 | 50 | 50 | 75 | 50 | 50 | 50 |
| $(NH_4)_2SO_4$ | — | — | — | — | — | — | 5 | — | — |
| $NaHCO_3$ | — | — | — | — | — | — | — | 5 | — |
| Carbon Black | — | — | — | — | — | — | — | — | 5 |

Cobalt loss from an immersed pellet into demineralized water was measured in accordance with the technique prescribed by Pyatnitskii ("Analytical Chemistry of the Elements," p. 130, Humphrey Science Pub. Co., Ann Arbor, Mich. 1969). Emission rate over the immersion period from day 7 to day 30 and other pertinent data is shown below:

| Formulation No. | Emmission Rate (per day) | Remarks |
|---|---|---|
| 13-E | 0.13% | Low density polyethylene (703) matrix no porosigen, 12.2% total cobalt content (W/W) |
| 13-C | 0.29% | Low density polyethylene (718) matrix, no porosigen 14.4% total cobalt content (W/W) |
| 13-A | 0.24% | Vistalon 702 EPM matrix modified with LDPE 718. Only 5.9% total cobalt content (W/W) No porosigen. |
| 13-B | 0.39% | Vistalon 702 EPM matrix modified with LDPE 718 but with a higher (12.3%) total cobalt content. No porosigen. |
| 13-D | 0.53% | EVA 763 matrix, no porosigen. Total cobalt content 10.4% (W/W). |
| 13-F | 0.69% | EVA 763 matrix, no porosigen. Higher total cobalt content, 12.1% (W/W). |
| 13-I | 0.90% | EVA 763 matrix with carbon black as an additive to increase free volume. |
| 13-G | 0.95% | EVA 763 matrix with ammonium sulfate additive as a porosigen. |
| 13-H | 1.05% | EVA 763 matrix with sodium bicarbonate as a porisigen. |

Cobalt sulfate is a highly soluble material (60.4 g/100 g cold water) and thus essentially serves a porosigenic function in LDPE so that emission is possible.

EXAMPLE XIV—CONTROLLED RELEASE SELENIUM MATERIALS

The following controlled release materials, using sodium selenate as the agent, were prepared and immersed in dimineralized water.

TABLE XIV

| Ingredient | Formulation No. | | | |
|---|---|---|---|---|
| | 14-A | 14-B | 14-C | 14-D |
| LDPE 718 | 25 | 25 | 25 | 25 |
| EVA 763 | — | 25 | — | 25 |
| Vistalon 702 | 25 | — | 25 | — |
| Zinc Stearate | 1 | 1 | 1 | 1 |
| $Na_2SeO_4$ | 25 | 25 | 25 | 25 |
| $(NH_4)_2SO_4$ | — | — | 2 | — |
| $NaHCO_3$ | — | — | — | 2 |

In accordance with agricultural needs, release rates are very low as measured over a 120-day period in demineralized water.

| 14-A | 0.0071% Se emission per day |
|---|---|
| 14-B | 0.0066% Se emission per day |
| 14-C | 0.0053% Se emission per day |
| 14-D | 0.0055% Se emission per day |

EXAMPLES XV—CONTROLLED RELEASE MAGNESIUM FORMULATIONS

Recipes for several typical magnesium emitters are shown below:

TABLE XV

| Ingredient | Formulation No. | | |
|---|---|---|---|
| | 15-A | 15-B | 15-C |
| Vistalon 702 | 25 | — | 25 |
| EVA 763 | — | 50 | — |
| LSPE 718 | 25 | — | 25 |
| Zinc Stearate | 1 | 1 | 1 |
| $Mg\ CO_3$ | 15 | 15 | — |
| $Mg\ SO_4$ | — | — | 15 |

Release in demineralized water was measured periodically and a rate of 0.15%/day (15-A), 0.09%/day (15-B), and 0.48%/day (15-C) noted. Magnesium analysis was performed by the method described in Flaschka, H. A., et al., Quantitative Analytical Chemistry, Vol. II, p. 140, Harper and Row, pub. Inc. N.Y., 1969.

EXAMPLE XVI—MULTIPLE ELEMENT RELEASE

With proper compounding, it is possible to release two or more elements simultaneously from the same matrix. In treating soil, that is cobalt poor, and which also requires a small supplement of zinc and iron formulation (16), shown below, can be utilized.

TABLE XVI

| Ingredient | Recipe |
|---|---|
| EVA 763 | 100 |
| Zinc Stearate | 1 |
| Cobalt Sulfate* | 25 |

TABLE XVI-continued

| Ingredient | Recipe |
| --- | --- |
| Iron Oxide** | 25 |
| Zinc Oxide*** | 10 |

*CoSO$_4$ . 7H$_2$O
**Fe$_2$O$_3$
***ZnO

A daily loss rate of 0.25%/day cobalt, 0.002%/day iron and 0.01%/day zinc was measured.

Multiple emission from one matrix can thus be accomplished and a material tailored to meet specific soil needs in some instances. It is, however, more likely that a given trace element's need can be met by appropriately mixing the proper proportion of different emitters (i.e. different matrices) during application to a given soil.

While in accordance with the patent statutes, only the preferred embodiments of the invention have been described in detail, therefore, for the true scope of the invention, reference should be had to the appended claims.

What is claimed is:

1. A controlled release plant nutrient dispenser comprising: a uniformly dispersed admixture of a plant nutrient, a porosigen, and 100 parts by weight of a polymer matrix, said polymer matrix made from a compound selected from the class consisting of an ethylene-vinyl acetate copolymer, an ethylene-propylene copolymer, a low density polyethylene, and combinations thereof;

the amount by weight of said ethylene constituent in said ethylene-vinyl acetate copolymer ranging from about 60 percent to about 95 percent, the weight average molecular weight of said ethylene-vinyl acetate copolymer ranging from about 40,000 to about 400,000;

the amount by weight of said ethylene constituent in said ethylene-propylene copolymer ranging from about 30 percent to about 75 percent, the weight average molecular weight of said ethylene-propylene copolymer ranging from about 50,000 to about 250,000;

said plant nutrient being required in minute amounts by a plant, the amount of said plant nutrient ranging from about 10 to about 160 parts by weight per 100 parts of said polymer matrix, the amount of said porosigen ranging from about 0.1 to about 70 parts by weight per 100 parts of said polymer matrix, said porosigen having a solubility of less than 100 grams per 100 grams of water so that upon contact of said dispenser with soil moisture, the plant nutrient is released at a rate required by the plant to stimulate growth.

2. A process of adding a controlled release plant nutrient mixture to a soil, comprising applying the controlled release plant nutrient mixture of claim 1 to the moist soil.

3. A controlled release plant nutrient dispenser according to claim 1, said plant nutrient selected from the group consisting of zinc, copper, iron, manganese, boron, molybdenum, cobalt, selenium, magnesium, and combinations thereof.

4. A process of adding a controlled release plant nutrient mixture to a soil, comprising applying the controlled release plant nutrient mixture of claim 3 to the moist soil.

5. A controlled release plant nutrient according to claim 3, wherein said ethylenepropylene copolymer has a melt flow index of from about 15 to about 45, wherein said ethylene-vinyl acetate has a melt flow index of from about 6 to about 12, and wherein said low density polyethylene has a melt flow index of from about 1 to about 25.

6. A controlled release plant nutrient according to claim 5, wherein the amount of said plant nutrient compound ranges from about 25 parts to about 125 parts.

7. A controlled release plant nutrient according to claim 6, wherein the amount of said porosigen ranges from about 1.0 to about 30 parts by weight.

8. A controlled release plant nutrient according to claim 7, wherein the amount of ethylene by weight in said ethylene-vinyl acetate copolymer ranges from about 80 percent to about 93 percent, wherein the amount of ethylene in said ethylene-propylene copolymer ranges from about 45 to about 75 percent by weight.

9. A controlled release plant nutrient according to claim 8, wherein the amount of said plant nutrient compound ranges from about 50 parts to about 100 parts, and wherein the amount of porosigen ranges from about 2.0 to about 12 parts by weight.

10. A controlled released plant nutrient according to claim 3, 5, 6, 7, 8 or 9, wherein said porosigen has a solubility of less than 0.1 grams per 100 grams of water and is a compound and the various hydrates thereof having said solubility wherein the cation of said compound is selected from the group consisting of the alkaline metals, the alkaline earth metals, nickel, iron, zinc, silver, and tin, and wherein said compound has an anion selected from the group consisting of an oxide, a carbonate, bicarbonate, nitrate, nitrite, nitride, phosphate, phosphite, phosphide, sulfate, sulfite, sulfide, and combinations thereof.

11. A controlled release plant nutrient mixture according to claim 10, wherein said moisture slowly removes said porosigen through dissolution and creates a porous network so that a plant nutrient within said mixture is released.

12. A process of adding a controlled release plant nutrient mixture to a soil, comprising applying the controlled release plant nutrient mixture of claim 10 to the moist soil.

13. A slow release trace nutrient composition according to claim 10, wherein said trace nutrient is a compound selected from the class consisting of zinc sulfate, zinc chloride, zinc carbonate, zinc oxide, zinc phosphate, zinc chlorate, zinc nitrate, the various hydrates of said zinc compounds, copper sulfate, copper carbonate, copper oxide, copper oxychloride, copper nitrate, copper phosphate, the various hydrates of said copper compounds, iron chloride, iron sulfate, iron oxide, the various hydrates of said iron compounds, manganese oxide, manganese sulfate, manganese chloride, manganese nitrate, the various hydrates of said manganese compounds, boric acid, sodium biborate, the various hydrates of said boron compounds, molybdenum oxide, sodium molybdate, potassium molybdate, the various hydrates of said molybdenum compounds, cobalt sulfate, cobalt chlorate, cobalt nitrate, the various hydrates of said cobalt compounds, sodium selenate, selenium dioxide, selenium trioxide, selenium oxychloride, selenium disulfide, selenium sulfur oxide, magnesium carbonate, magnesium sulfate, magnesium nitrate, magnesium acetate, magnesium oxide, magnesium phosphate, magnesium sulfite, and the various hydrates of said magnesium compounds and combinations thereof.

14. A slow release trace nutrient composition according to claim 13, wherein said trace nutrient is a compound selected from the class consisting of zinc sulfate, zinc chloride, zinc carbonate, zinc oxide, copper sulfate, copper carbonate, copper oxide, copper oxychloride, iron chloride, iron sulfate, iron oxide, manganese oxide, manganese sulfate, manganese chloride, boric acid, sodium biborate, molybdenum oxide, sodium molybdate, cobalt sulfate, sodium selenate, magnesium carbonate, and magnesium sulfate and combinations thereof.

15. A slow release trace nutrient composition according to claim 14, wherein said porosigen is calcium carbonate.

16. A controlled release plant nutrient mixture according to claim 15, wherein said moisture slowly removes said porosigen through dissolution and creates a porous network so that a plant nutrient within said mixture is released.

17. A process of adding a controlled release plant nutrient mixture to a soil, comprising applying the controlled release plant nutrient mixture of claim 13 to the moist soil.

18. A slow release trace nutrient composition according to claim 3, 5, 6, 7, 8 or 9, wherein said porosigen has a solubility of from about 0.1 to about 100 grams per 100 grams of water and is a compound and the various hydrates thereof having such a solubility selected from the group consisting of the halogenated alkaline metals, the halogenated alkaline earth metals, halogenated nickel, halogenated tin, halogenated silver, ammonium bromide, ammonium carbonate, ammonium bicarbonate, ammonium chlorate, ammonium chlorite, ammonium chloride, ammonium fluoride, ammonium sulfate, sodium carbonate, sodium bicarbonate, sodium silicate, and silicon dioxide.

19. A controlled release plant nutrient mixture according to claim 18, wherein said moisture slowly removes said porosigen through dissolution and creates a porous network so that a plant nutrient within said mixture is released.

20. A process of adding a controlled release plant nutrient mixture to a soil, comprising applying the controlled release plant nutrient mixture of claim 18 to the moist soil.

21. A controlled release plant nutrient according to claim 18, wherein said trace nutrient is a compound selected from the class consisting of zinc sulfate, zinc chloride, zinc carbonate, zinc oxide, zinc phosphate, zinc chlorate, zinc nitrate, the various hydrates of said zinc compounds, copper sulfate, copper carbonate, copper oxide, copper oxychloride, copper nitrate, copper phosphate, the various hydrates of said copper compounds, iron chloride, iron sulfate, iron oxide, the various hydrates of said iron compounds, manganese oxide, manganese sulfate, manganese chloride, manganese nitrate, the various hydrates of said manganese compounds, boric acid, sodium biborate, the various hydrates of said boron compounds, molybdenum oxide, sodium molybdate, potassium molybdate, the various hydrates of said molybdenum compounds, cobalt sulfate, cobalt chlorate, cobalt nitrate, the various hydrates of said cobalt compounds, sodium selenate, selenium dioxide, selenium trioxide, selenium oxychloride, selenium disulfide, selenium sulfur oxide, magnesium carbonate, magnesium sulfate, magnesium nitrate, magnesium acetate, magnesium oxide, magnesium phosphate, magnesium sulfite, and the various hydrates of said magnesium compounds and combinations of.

22. A controlled release plant nutrient according to claim 21, wherein said trace nutrient is a compound selected from the class consisting of zinc sulfate, zinc chloride, zinc carbonate, zinc oxide, copper sulfate, copper carbonate, copper oxide, copper oxychloride, iron chloride, iron sulfate, iron oxide, manganese oxide, manganese sulfate, manganese chloride, boric acid, sodium biborate, molybdenum oxide, sodium molybdate, cobalt sulfate, sodium selenate, magnesium carbonate, and magnesium sulfate and combinations thereof.

23. A controlled release plant nutrient according to claim 22, wherein said porosigen is selected from the class consisting of ammonium sulfate, sodium bicarbonate, sodium carbonate and sodium silicate.

24. A controlled release plant nutrient mixture according to claim 23, wherein said moisture slowly removes said porosigen through dissolution and creates a porous network so that a plant nutrient within said mixture is released.

25. A process of adding a controlled release plant nutrient mixture to a soil, comprising applying the controlled release plant nutrient mixture of claim 21 to the moist soil.

* * * * *